US012758097B2

(12) United States Patent
Xereas et al.

(10) Patent No.: US 12,758,097 B2
(45) Date of Patent: Oct. 13, 2026

(54) IMPLANTABLE SENSOR ASSEMBLY INCLUDING A SENSOR AND A COMPLIANT STRUCTURE

(71) Applicant: MY01 IP HOLDINGS INC., Montreal (CA)

(72) Inventors: George Xereas, Montreal (CA); Charles Allan, Montreal (CA); Mohamad Nizar Kezzo, Montreal (CA); Vahid Tayari, Montreal (CA); Christopher Benn Agellon, Baie d'Urfe (CA); Edward J. Harvey, Westmount (CA); Animesh Saha Shovan, Montreal (CA)

( * ) Notice: Subject to any disclaimer, the term of this patent is extended or adjusted under 35 U.S.C. 154(b) by 963 days.

(21) Appl. No.: 17/791,677

(22) PCT Filed: Jan. 15, 2021

(86) PCT No.: PCT/CA2021/050041

§ 371 (c)(1),
(2) Date: Jul. 8, 2022

(87) PCT Pub. No.: WO2021/142546

PCT Pub. Date: Jul. 22, 2021

(65) Prior Publication Data

US 2023/0037844 A1 Feb. 9, 2023

Related U.S. Application Data

(60) Provisional application No. 62/962,400, filed on Jan. 17, 2020.

(51) Int. Cl.
*A61B 5/00* (2006.01)

(52) U.S. Cl.
CPC ...... *A61B 5/0031* (2013.01); *A61B 2562/182* (2013.01)

(58) Field of Classification Search
None
See application file for complete search history.

(56) References Cited

U.S. PATENT DOCUMENTS 5,918,110 A 6/1999 Abraham-Fuchs et al.
7,073,375 B2 7/2006 Parker et al.
(Continued)

FOREIGN PATENT DOCUMENTS

CA 3056558 A1 9/2018
CN 107818957 A 3/2018
(Continued)

OTHER PUBLICATIONS

International Search Report and Written Opinion issuef in corresponding application No. PCT/CA2021/050041 on Mar. 23, 2021.
(Continued)

*Primary Examiner* — Matthew Eric Ogles
(74) *Attorney, Agent, or Firm* — Anglehart et al.

(57) ABSTRACT

An implantable sensor assembly comprises a support structure including a board, a compliant structure disposed on a top surface of the board, and a sensor supported by the compliant structure above the top surface of the board. An aperture is formed in the support structure for exposing at least in part a face of the sensor. The sensor may be a pressure sensor having a sensing membrane exposed through the aperture formed in the support structure. A stiffener, which may be conductive, may be mounted to a bottom surface of the board. The sensor and other components may be covered by a polymer shell having a conductive cover or by a gel contained within a rigid cap, which may be conductive. An electromagnetic shield may be formed by an electrical connection between the conductive cover or the conductive rigid cap and the conductive stiffener.

13 Claims, 7 Drawing Sheets

(56) References Cited

U.S. PATENT DOCUMENTS

| | | | | |
|---|---|---|---|---|
| 9,945,747 | B1 | 4/2018 | Kusanale et al. | |
| 10,499,822 | B2 | 12/2019 | Harvey et al. | |
| 2005/0049499 | A1 | 3/2005 | Kaplan | |
| 2005/0181012 | A1* | 8/2005 | Saint | A61N 1/37512 600/300 |
| 2007/0118039 | A1 | 5/2007 | Bodecker et al. | |
| 2010/0174201 | A1* | 7/2010 | Bodecker | A61B 5/6882 600/488 |
| 2012/0071782 | A1* | 3/2012 | Patil | A61B 5/0538 702/65 |
| 2013/0248345 | A1* | 9/2013 | Haag | H01H 11/04 200/600 |
| 2014/0187876 | A1* | 7/2014 | Ohkoshi | A61B 5/0031 600/300 |
| 2014/0238153 | A1* | 8/2014 | Wood | A43B 23/029 73/862.627 |
| 2015/0173215 | A1* | 6/2015 | Rickert | B23K 1/0008 228/208 |
| 2015/0230907 | A1* | 8/2015 | Grewe | A61F 2/012 606/200 |
| 2015/0351648 | A1* | 12/2015 | Harvey | A61B 5/076 600/561 |
| 2017/0056674 | A1* | 3/2017 | Bortolin | A61N 1/3968 |
| 2019/0380628 | A1* | 12/2019 | Routh | G16H 80/00 |

FOREIGN PATENT DOCUMENTS

| | | | |
|---|---|---|---|
| CN | 110141210 | A | 8/2019 |
| CN | 110402098 | A | 11/2019 |
| EP | 2378059 | A1 | 10/2011 |
| WO | 2018140983 | A1 | 8/2018 |
| WO | 2018167693 | A1 | 9/2018 |
| WO | 2018185032 | A1 | 10/2018 |

OTHER PUBLICATIONS

Examiner's Report issued by the Canadian Intellectual Property Office on Sep. 7, 2023 in connection with Canadian patent application No. 3,164,141, 4 pages.

Examiner's Report issued by the Canadian Intellectual Property Office on May 27, 2024 in connection with Canadian patent application No. 3,164,141, 5 pages.

European Search Report issued by the European Patent Office on Dec. 11, 2023 in connection with European patent application No. 21741160.2, 8 pages.

Xue et al., "Highly Integrated MEMS-ASIC Sensing System for Intracorporeal Physiological Condition Monitoring", Sensors, vol. 18, No. 2, Jan. 2, 2019.

European Examination Report issued by European Patent Office on Sep. 12, 2025 in connection with European patent application No. 21741160.2.

Corresponding Canadian patent application No. 3,164,141 examination report dated Nov. 28, 2025.

Corresponding Chinese patent application No. 202180022556.9 examination report dated Nov. 4, 2024. (machine translation provided).

* cited by examiner

IMPLANTABLE SENSOR ASSEMBLY INCLUDING A SENSOR AND A COMPLIANT STRUCTURE

CROSS-REFERENCE

The present application claims priority from U.S. Provisional Application Ser. No. 62/962,400, filed on Jan. 17, 2020, the entirety of which is incorporated by reference herein.

TECHNICAL FIELD

The present disclosure relates to the field of implantable sensors. More specifically, the present disclosure relates to an implantable sensor assembly.

BACKGROUND

Implantable biocompatible sensors are adapted to be inserted under a subject's skin in order to measure and collect data related to physical conditions of the subject body. Implantable biocompatible sensors have undergone extensive improvements over the years and find a variety of applications for offering a rapid and accurate way for doctors, nurses and caregivers to monitor subjects with particular medical conditions.

An example of a method and system for installing a sensor in a body is provided in United States Patent Application Publication No. 2020/0360050 A1 to Harvey et al., published on Nov. 19, 2020, the disclosure of which is incorporated by reference herein.

Once a sensor is in place under the skin of patient, it may provide measurements to an external module via signals that propagate, for example, through a cable. The sensor is exposed to various physical conditions that prevail in the body, for example conditions of temperature, humidity, pressure, potential hydrogen (pH), and the like. The sensor may be adapted to measure one of these conditions, but its measurements may be altered by the other of these conditions.

Therefore, there is a need for improvements in implantable biocompatible sensors.

SUMMARY

In one aspect, various implementations of the present technology provide an implantable sensor assembly, comprising: a support structure comprising a board; a compliant structure disposed on a top surface of the board; a sensor supported by the compliant structure above the top surface of the board; and an aperture formed in the support structure for exposing at least in part a face of the sensor.

In some implementations of the present technology, the compliant structure comprises: a first portion formed of a first gel compound disposed on a first face of the sensor; and a second portion formed of a second gel compound surrounding the sensor and extending between the first gel compound and the exposed face of the sensor.

In some implementations of the present technology, the first gel compound has a first viscosity and the second gel compound has a second viscosity greater than the first viscosity.

In some implementations of the present technology, the sensor assembly further comprises a polymer shell applied on the top surface of the board, the polymer shell enclosing the sensor and the compliant structure.

In some implementations of the present technology, the sensor assembly further comprises at least one surface mounted technology (SMT) component mounted on the board and operatively connected to the sensor; and a cable extending from the at least one SMT component and adapted to communicate measurements from the sensor to an external device.

In some implementations of the present technology, the at least one SMT component comprises a converter adapted to convert the measurements from the sensor into digital signals.

In some implementations of the present technology, the sensor assembly further comprises comprising a polymer shell applied on the top surface of the board, the polymer shell enclosing the at least one SMT component, the sensor and the compliant structure.

In some implementations of the present technology, the polymer shell is an epoxy shell.

In some implementations of the present technology, the sensor assembly further comprises a conductive cover applied on the polymer shell.

In some implementations of the present technology, the conductive cover comprises a layer of conductive ink.

In some implementations of the present technology, the compliant structure fully covers all faces of the sensor other than the exposed face of the sensor while allowing passages of electrical connections between the sensor to the at least one SMT component.

In some implementations of the present technology, electrical connections between the at least one SMT component and the sensor each comprise one or more elements selected from wire bonds, solder paste traces on the board, conductive ink traces on the board, and a combination thereof.

In some implementations of the present technology, the sensor is a pressure sensor comprising a sensing membrane exposed at least in part to the aperture formed in the support structure.

In some implementations of the present technology, the sensor assembly further comprises a layer of hydrophobic material disposed on the sensing membrane.

In some implementations of the present technology, the support structure further comprises a stiffener mounted on a bottom surface of the board.

In some implementations of the present technology, the sensor assembly further comprises a conductive cover, wherein: the stiffener is made of a conductive material; and the stiffener is electrically connected to the conductive cover.

In some implementations of the present technology, the conductive cover comprises a layer of conductive ink.

In some implementations of the present technology, the stiffener has a hook hole adapted for mating with a hook of an insertion device.

In some implementations of the present technology, the support structure further comprises a cap enclosing the board, the compliant structure and the sensor.

In some implementations of the present technology, the support structure further comprises a stiffener mounted on a bottom surface of the board; the cap and the stiffener are each made of conductive material; and the stiffener is electrically connected to the cap.

In some implementations of the present technology, the cap includes one or more holes providing access to a cavity formed between the top surface of the board and the cap.

In some implementations of the present technology, the cavity formed between the top surface of the board and the cap is filled at least in part with a gel.

In some implementations of the present technology, the board has a through aperture between its top surface and its bottom surface; and the sensor is mounted above the top surface of the board so that a bottom face of the sensor is exposed at least in part to the through aperture of the board.

In some implementations of the present technology, the compliant structure covers faces of the sensor other than the bottom face of the sensor exposed to the through aperture of the board.

In some implementations of the present technology, the bottom face of the sensor comprises a perimeter and a central area, the sensor being mounted above the top surface of the board so that the central area of the bottom face of the sensor is positioned above the through aperture of the board; and the compliant structure forms an interface between the perimeter of the bottom face of the sensor and the top surface of the board, the compliant structure covering at least in part faces of the sensor other than the central area of the bottom face of the sensor.

In some implementations of the present technology, the support structure further comprises a stiffener mounted on the bottom surface of the board.

In some implementations of the present technology, the stiffener has a through aperture aligned with the through aperture of the board, whereby the sensing membrane is exposed at least in part to the through aperture of the stiffener.

In some implementations of the present technology, the stiffener has a hook hole adapted for mating with a hook of an insertion device.

In some implementations of the present technology, the sensor assembly further comprises a conductive cover, wherein: the stiffener is made of a conductive material; and the stiffener is electrically connected to the conductive cover.

In some implementations of the present technology, the conductive cover comprises a layer of conductive ink.

In some implementations of the present technology, the support structure further comprises a cap enclosing the board, the compliant structure and the sensor.

In some implementations of the present technology, the cap and the stiffener are each made of conductive material; and the stiffener is electrically connected to the cap.

In some implementations of the present technology, the cap includes one or more holes providing access to a cavity formed between the top surface of the board and the cap.

In some implementations of the present technology, the cavity formed between the top surface of the board and the cap is filled at least in part with a gel.

In some implementations of the present technology, the sensor assembly further comprises a cap enclosing the board, the compliant structure and the sensor, the cap comprising a top aperture for exposing at least in part a top surface of the sensor.

In some implementations of the present technology, the sensor assembly further comprises a stiffener mounted on a bottom surface of the board.

In some implementations of the present technology, the cap and the stiffener are each made of conductive material; and the stiffener is electrically connected to the cap.

In some implementations of the present technology, the cap includes one or more holes providing access to a cavity formed between the top surface of the board and the cap.

In some implementations of the present technology, the cavity formed between the top surface of the board and the cap is filled at least in part with a gel.

In another aspect, various implementations of the present technology provide an implantable sensor assembly, comprising: a board; a sensor mounted on a top surface of the board; a polymer shell applied on the top surface of the board, the polymer shell enclosing the sensor; a conductive cover applied on the polymer shell; a stiffener made of a conductive material and mounted on a bottom surface of the board; and an electrical connection between the stiffener and the conductive cover.

In some implementations of the present technology, the sensor assembly further comprises at least one surface mounted technology (SMT) component mounted on the board and operatively connected to the sensor; and a cable extending from the at least one SMT component and adapted to communicate measurements from the sensor to an external device.

In some implementations of the present technology, the at least one SMT component comprises a converter adapted to convert the measurements from the sensor into digital signals.

In some implementations of the present technology, the at least one SMT component is enclosed by the polymer shell.

In some implementations of the present technology, electrical connections between the at least one SMT component and the sensor comprise one or more elements selected from wire bonds, solder paste traces on the board, conductive ink traces on the board, and a combination thereof.

In some implementations of the present technology, the stiffener has a hook hole adapted for mating with a hook of an insertion device.

In some implementations of the present technology, the conductive cover comprises a layer of conductive ink.

In a further aspect, various implementations of the present technology provide an implantable sensor assembly, comprising: a board; a sensor mounted on a top surface of the board; a cap enclosing the board and the sensor; and a stiffener mounted on a bottom surface of the board.

In some implementations of the present technology, the board has a through aperture between its top surface and its bottom surface.

In some implementations of the present technology, the sensor is mounted above the top surface of the board; the stiffener has a through aperture aligned with the through aperture of the board; and a sensing membrane on a bottom face of the sensor of the sensor is exposed at least in part to the through aperture of the board.

In some implementations of the present technology, the sensor assembly further comprises a layer of hydrophobic material disposed on the sensing membrane.

In some implementations of the present technology, the cap and the stiffener are each made of conductive material; and the stiffener is electrically connected to the cap.

In some implementations of the present technology, the cap includes one or more holes providing access to a cavity formed between the top surface of the board and the cap.

In some implementations of the present technology, the cavity formed between the top surface of the board and the cap is filled at least in part with a gel.

In some implementations of the present technology, the sensor assembly further comprises at least one surface mounted technology (SMT) component mounted on the board and operatively connected to the sensor; and a cable extending from the at least one SMT component and adapted to communicate measurements from the sensor to an external device.

In some implementations of the present technology, the at least one SMT component comprises a converter adapted to convert the measurements from the sensor into digital signals.

In some implementations of the present technology, the at least one SMT component is enclosed by the cap.

In some implementations of the present technology, electrical connections between the at least one SMT component and the sensor comprise one or more elements selected from wire bonds, solder paste traces on the board, conductive ink traces on the board, and a combination thereof.

In some implementations of the present technology, the stiffener has a hook hole adapted for mating with a hook of an insertion device.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which.

Like numerals represent like features on the various drawings.

DETAILED DESCRIPTION

Figure 1:
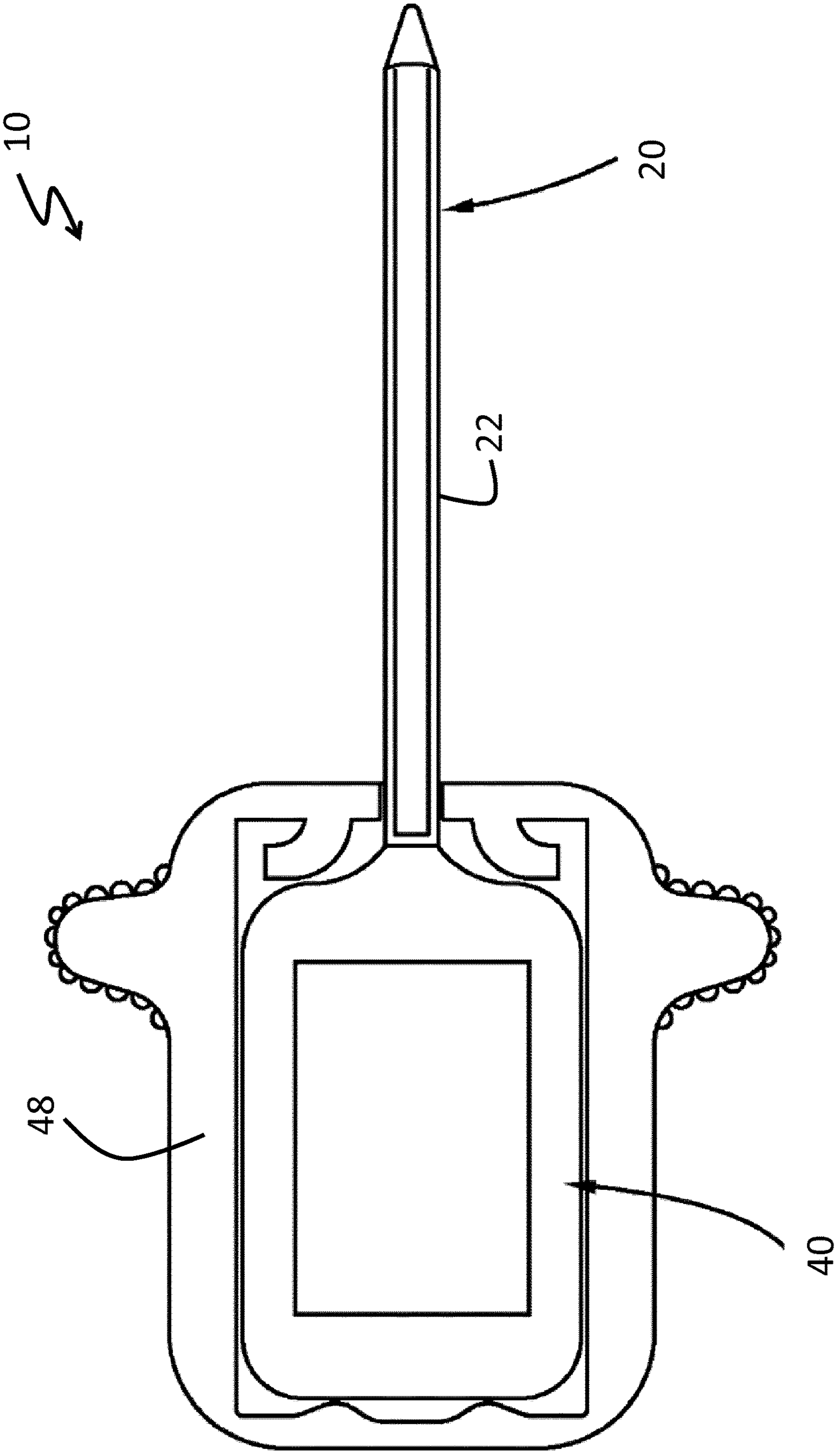
FIG. 1 is a top view of a system for installing a sensor comprising a puncture device and a sensor assembly according to an embodiment.

Various aspects of the present disclosure generally address one or more of the problems caused by the exposure of implantable biocompatible sensors to various physical conditions.

When implanted in a body, a sensor is subject to various conditions that might impact its measurement capabilities. Developers have noted that the sensor and a supporting structure for the sensor may expand at different rates as the temperature of the sensor and of its supporting structure is modified by insertion in the body. This may cause a stress on the sensor and impact its capability to measure parameters of the body. For example, a sensor of a pressure in the area of insertion in the body might lose sensitivity as stresses caused by the different expansion rates for the sensor and for its supporting structure might not be distinguishable from the actual pressure within the body. In another example, a change of dielectric constant from before to after the insertion may adversely affect a measurement signal generated by the sensor.

In a first aspect, an implantable sensor assembly comprises a sensor mounted on a board. Faces of the sensor that are not directly applied on the board are covered by a compliant structure. As the sensor, the board and other components of the sensor assembly react to a change of temperature caused by the insertion of the sensor assembly in the body, causing a stress that propagates throughout the sensor assembly, some degree of flexibility in the compliant structure isolates the sensor from this stress.

In a second aspect, external components of the sensor assembly are made of conductive materials, including a top conductive cover and a bottom conductive stiffener. The conductive cover and the stiffener are electrically connected and thus form an electromagnetic shield surrounding the sensor assembly. The conductive cover forms a Faraday-like shield that minimizes a sensitivity of the sensor to variations in a dielectric constant of its environment. A dielectric change would manifest as an offset between values measured by the sensor assembly and true values. Although this electromagnetic shield is not expected to form a perfect Faraday cage, parasitic effects caused by chemical conditions in the body, that might otherwise impact the sensitivity of the sensor, are substantially reduced or eliminated in certain embodiments.

Additional details of the construction of the insertable sensor assembly and of its various embodiments will be described in relation to the following drawings. In the drawings, the term "forward end" refers to an end of the sensor assembly that is first inserted when in use and the term "rear end" refers to an opposite end of the sensor assembly. The terms "upper", "lower", "top" and "bottom" are relative terms defined in relation to the drawings. The skilled reader will appreciate that, in use, the sensor assembly may be implanted sideways or upside down in a body. Unless otherwise noted, the drawings are not to scale.

Figure 2:
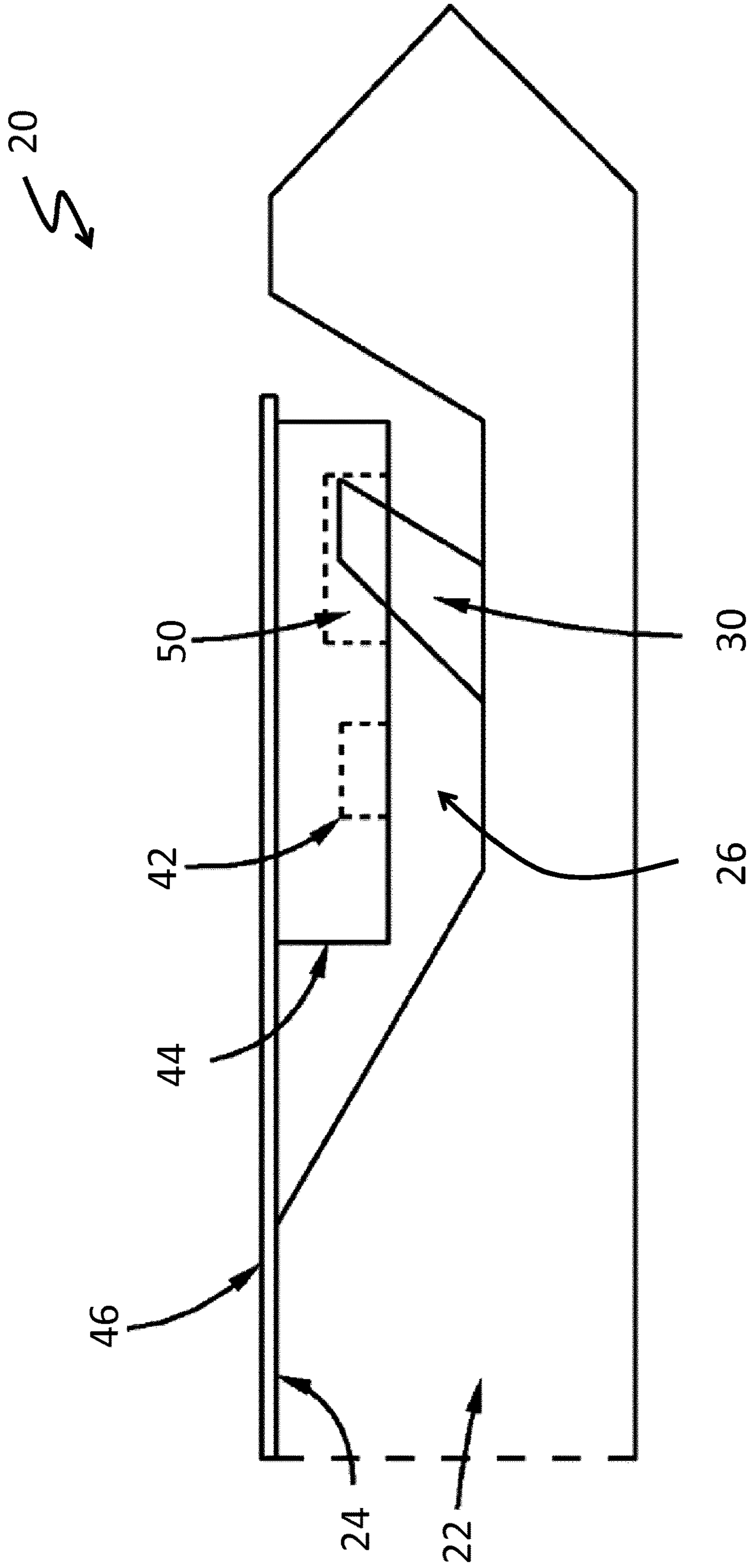
FIG. 2 is an enlarged left side cross-sectional view of a puncturing end of the puncture device of FIG. 1 having a sensor body installed on an anchoring pin according to an embodiment.

FIG. 1 is a top view of a system for installing a sensor comprising a puncture device and a sensor assembly, as disclosed by Harvey in US 2020/0360050 A1. FIG. 2 is an enlarged left side cross-sectional view of a puncturing end of the puncture device of FIG. 1 having a sensor body installed on an anchoring pin. Referring to FIGS. 1 and 2, a system 10 is useable for installing a sensor under the skin of a body. In the illustrated embodiment, the system 10 comprises a puncture device 20 and a sensor assembly 40. The puncture device 20 comprises an elongated member 22 adapted to penetrate under a body's skin for installing a sensor 42. The elongated member 22 has an upper surface 24 on which a sensor body 44 may rest so that a cable 46 connecting the sensor 42 to an external module 48 of the sensor assembly 40 is placed generally in parallel to the upper surface 24 of the elongated member 22. A recess 26 is dug in the upper surface 24 near a forward end 28 of the elongated member 22. An anchoring pin 30 is located within the recess 26 and is received in a cavity 50 of the sensor body 44 for securing the sensor body 44 of the sensor assembly 40 onto the upper surface 24 of the puncture device 20 prior to insertion of the assembly formed by the sensor body 44 and the forward end 28 of the elongated member 22 under the body's skin. Following insertion, the anchoring pin 30 may be disengaged from the cavity 50 of the sensor body 44 by rotating the elongated member 22. The elongated member 22 can then be pulled out from the body's skin, leaving the sensor body 44 in place, with the cable 46 connecting the sensor 42 to the external module 48 of the sensor assembly 40.

Once the sensor body 44 is in place under the body's skin, the sensor 42 may provide measurements captured by the sensor assembly 40 to the external module 48 via signals that propagate in the cable 46. The sensor 42 is exposed to various physical conditions that prevail in the body, for example conditions of temperature, humidity, pressure, potential hydrogen (pH), and the like. The sensor 42 may be adapted to measure one of these conditions, but such measurements may be altered by the other of these conditions.

Figures 3, 4, 5:
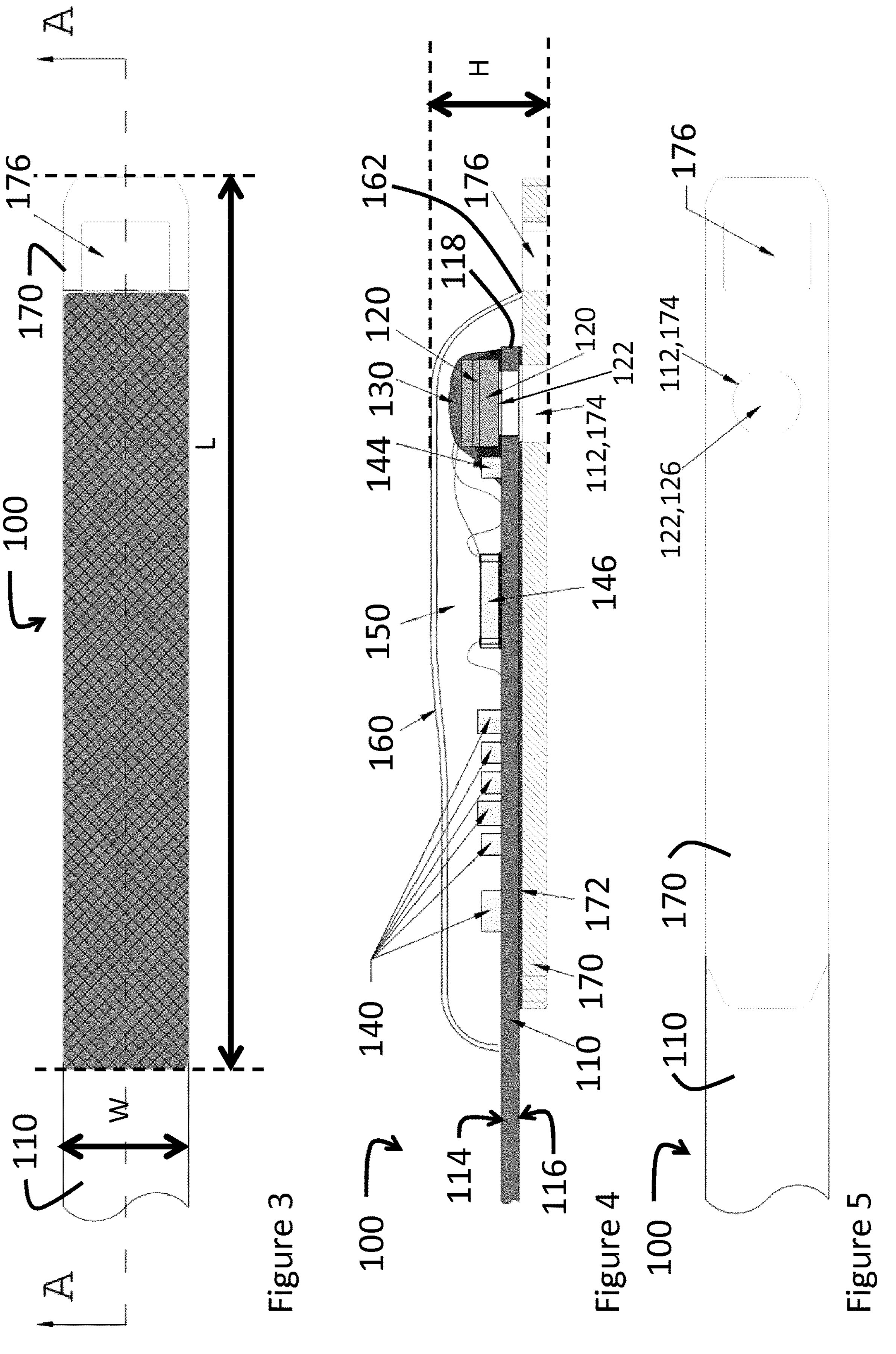
FIG. 3 is a top plan view of an implantable sensor assembly according to an embodiment.
FIG. 4 is a cross-sectional, side elevation view of the implantable sensor assembly of FIG. 2 according to an embodiment.
FIG. 5 is a bottom plan of the implantable sensor assembly of FIG. 2 according to an embodiment.
Figure 6:
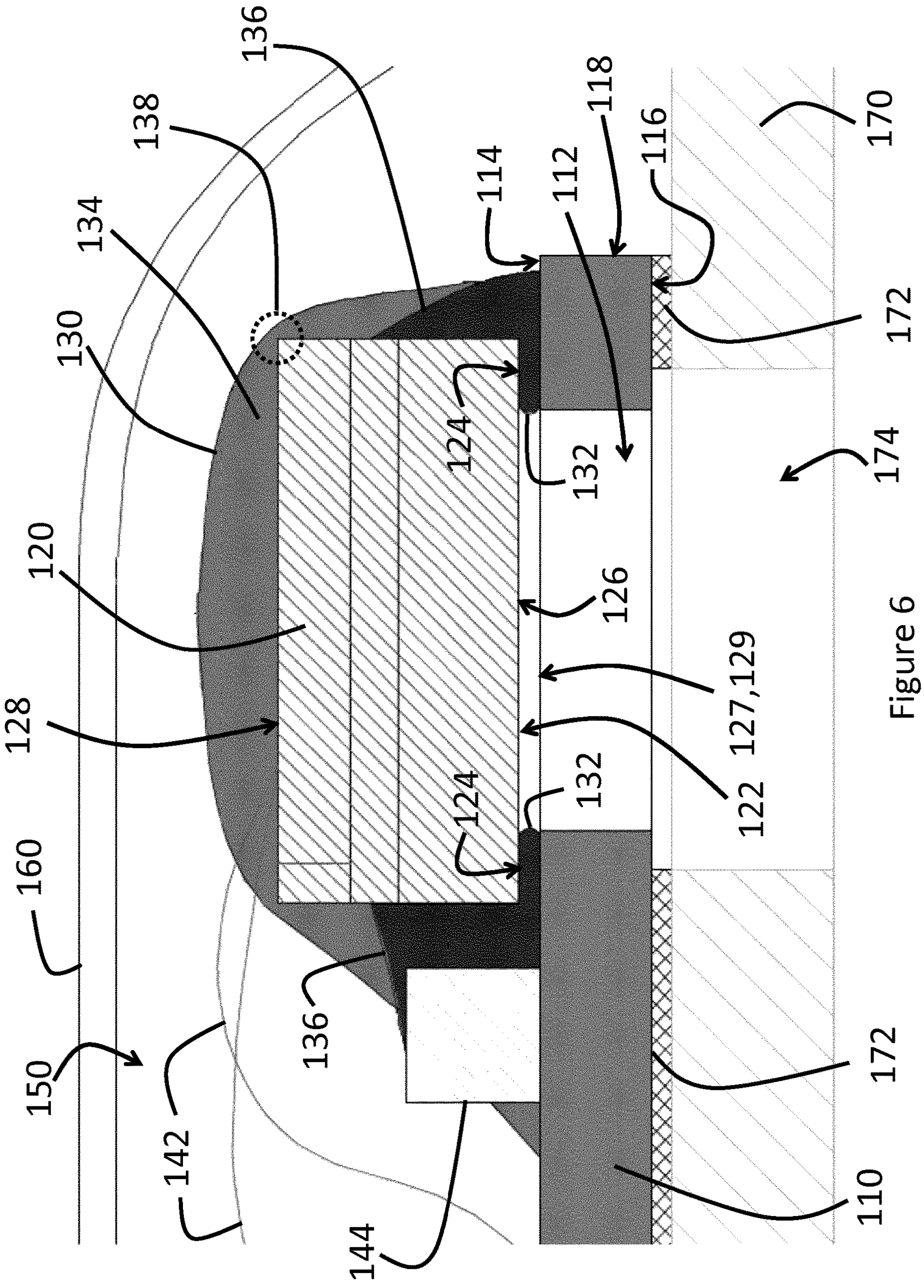
FIG. 6 is a detailed view of a compliant structure supporting a sensor according to an embodiment.

FIG. 3 is a top plan view of an implantable sensor assembly according to an embodiment. FIG. 4 is a cross-sectional, side elevation view of the implantable sensor assembly of FIG. 2. The cross-section view of FIG. 4 is taken along lines A-A of FIG. 3. FIG. 5 is a bottom plan of the implantable sensor assembly of FIG. 2. FIG. 6 is a detailed view of a compliant structure supporting a sensor according to an embodiment.

Referring to FIGS. 3, 4, 5 and 6, an implantable sensor assembly 100 comprises a support structure that includes for example a board 110, a polymer shell 150 and a stiffener 170. The sensor assembly 110 also comprises a sensor 120 mounted on the board 110, a compliant structure 130 formed over the sensor 120, a plurality of surface mounted technology (SMT) components 140. The polymer shell 150 may enclose the compliant structure 130 and the SMT components. A conductive cover 160 may be applied on the polymer shell 150. The stiffener 170 may be mounted underneath the board 110.

The board 110, for example a printed circuit board (PCB) made of polyimide, is generally shaped as an elongated rectangle. It includes a through aperture 112 between its top surface 114 and its bottom surface 116. The through aperture 112 may be circular, as shown in the non-limiting example of FIG. 5. The through aperture 112 is located near a forward-end 118 of the board 110. The sensor 120 and the SMT components 140 are mounted on the top surface 114 of the board 110. In particular, the sensor 120 has a bottom face 122 comprising a perimeter 124 and a central area 126 surrounded by the perimeter 124. The perimeter 124 located on the bottom face 122 is positioned slightly above the top surface 114 of the board so that the central area 126 of the bottom face 122 of the sensor 120 is positioned above the through aperture 112 of the board 110 and is exposed, at least in part, to the through aperture 112 of the board 110.

The compliant structure 130 is formed of one or more materials capable of elastic deformation. For example and without limitation, these materials may have a durometer level in a range between 0 and 80 on the Shore 00 Hardness Scale, or in a range between 0 and 50 on the Shore A Hardness Scale. Non-limiting examples of suitable materials include silicone gels, silicone rubbers, silicone adhesives, hydrogels and sol-gels. The compliant structure 130 supports the sensor 120 above the top surface 114 of the board 110. To this end, lips 132 of the compliant structure 130 extend between the perimeter 124 and the top surface 114 of the board 110 to form an interface between the perimeter 124 and the top surface 114 of the board 110. The compliant structure 130 covers at least in part faces of the sensor 120 other than the central area 126 of the bottom face 122 of the sensor 120 that is exposed to the through aperture 112.

The compliant structure 130 is configured to maintain the sensor 120 in place on the board 110, over the through aperture 112, with sufficient flexibility to isolate the sensor 120 from stresses present in the board 110 and in other parts of the sensor assembly 100. This flexibility is limited to prevent excessive movement of the sensor 120 caused by pressures transmitted on its bottom face 122 via the through aperture 112, such movements, if present, potentially affecting measurements provided by the sensor 120. The compliant structure 130 is also configured to decouple stresses that might otherwise be transmitted to the sensor 120 from the sensor assembly 100 as a whole and, particularly, from the polymer shell 150. When fabricating the sensor assembly 100, a material of the compliant structure 130 is poured over the sensor 120 with sufficient flowability to fully cover the sensor 120 before the formation of the polymer shell 150.

In an embodiment, the compliant structure 130 is constructed using at least two (2) distinct compounds in order to meet the above-mentioned characteristics. The enlarged view of FIG. 6 highlights that the compliant structure 130 may comprise an upper portion 134 formed of a first compound and a lower portion 136 formed of a second gel compound. In this embodiment, the upper portion 134 is made of a first gel compound, for example and without limitation a soft silicone gel such as a Gel-8251 from NuSil™, the first gel compound having a first viscosity, and the lower portion 136 is made of a second gel compound, for example and without limitation another soft silicone gel such as a MED2-4013 from NuSil™, the second gel compound having a second viscosity greater than the first viscosity.

In the embodiment of FIG. 6, the upper portion 134 of the structure 130 is disposed on a top face 128 of the sensor 120. In this embodiment, the upper portion 134 has a maximum thickness of about 0.2 mm. The lower portion 136 of the structure 130 surrounds the sensor 120 and extends between the upper portion 134 and the perimeter 124 of the bottom face 122 of the sensor 120. In the shown embodiment, the lips 132 are formed as continuations of the lower portion 136. The compliant structure 130 may be fairly thin in some areas, for example in areas 138 covering edges of the top face 128 of the sensor 120 where, in a non-limiting example, a minimum thickness of 0.1 mm should be preserved.

It may be noted that FIG. 6 shows that a SMT component 144 is partially enclosed by the compliant structure 130. This is an effect of the manufacturing process of the sensor assembly 100, in which the first and second gel compounds are applied in a controlled manner that may not prevent enclosing in part or in whole a component of the sensor assembly 100 that is proximate to the sensor 120. The SMT component 144 is not floating but is directly mounted on the top surface 114 of the board 110. Consequently, the SMT component 144 is expected to remain in a fixed position through the useful life of the sensor assembly 100.

The polymer shell 150 is applied on the top surface 114 of the board 110. The polymer shell 150 is initially applied as a liquid or viscous product so that it may fully enclose the compliant structure 130, including the sensor 120, and further enclose the SMT components 140 prior to hardening. The polymer shell may for example and without limitation be formed of a biocompatible epoxy such as LOCTITE-3894™. In an embodiment, the compliant structure 130 fully covers all faces of the sensor 120 other than the central area 126 of the bottom face 122 of the sensor 120, other than providing for the passages of wire bonds 142 connecting the sensor 120 to at least one of the SMT components 140, in order to prevent contact between the sensor 120 and the polymer shell 150. The compliant structure 130 may nevertheless be constructed so that it does not flow onto wire bonds (not shown) that connect the various SMT components 140 and so that it does not ooze beyond edges of the board 110.

Following insertion of the sensor assembly 100 in a body, the board 100, the polymer shell 150, and other components of the sensor assembly 100 may react to the heat of the body and expand in one or more dimensions. The compliant structure 130 provides some level of mechanical isolation between the sensor 120 and the other components of the sensor assembly 100. In this manner, stresses that could have been imposed on the sensor 120 by the thermal expansion of the board 110 or of the other components of the sensor assembly 100 are considerably reduced or even eliminated. Otherwise stated, the compliant structure 130 may be understood as allowing the sensor 120 to be floating within the sensor assembly 100. Of course, the viscosity of the first and second gel compounds is selected so that the sensor 120 only has a modest level of freedom to float within the sensor assembly 100, this level of freedom being sufficient to prevent the transfer of stress from the board 110 to the sensor 120.

The conductive cover 160 is applied on the polymer shell 150 and is intended to form at least a partial Faraday-like shield to absorb some of the parasitic effects caused by chemical conditions in the body in which the sensor assembly 100 is inserted, thereby preserving to some extent the sensitivity of the sensor 120. The conductive cover 160 may comprise a layer of conductive ink, for example and without limitation a 125-26 conductive ink from Creative Materials™, the conductive ink being applied on the polymer shell 150. The conductive ink may be thinned with methyl isobutyl ketone (MIBK) and spray coated over the polymer shell 150 up to a 0.2 mm thickness.

The stiffener 170 is mounted on the bottom surface 116 of the board 110. In the shown embodiment, a thin adhesive layer 172, for example a layer of conductive epoxy, is used to attach the stiffener 170 to the board 110. The stiffener 170 has a through aperture 174 that is substantially aligned with the through aperture 112 of the board 110 so that the central area 126 of the bottom face 122 of the sensor 120, which is exposed at least in part to the through aperture 112 of the board 110, is also exposed at least in part to the through aperture 174 of the stiffener 170.

The above-described arrangement provides that the central area 126 of the bottom face 122 of the sensor 120 is at least in part externally exposed from the sensor assembly 100 and is thus able to measure a physical condition of the body, when inserted. In an embodiment, the sensor 120 is a pressure sensor, for example micro-electro-mechanical systems (MEMS) device such as a SCB10H-B012FB capacitive pressure sensor from Murata™. In a non-limiting example, the sensor 120 may have an absolute pressure range of 650 to 900 mmHg with an accuracy of +/−0.2 mmHg, a resolution of +/−0.001 mmHg and a temperature sensitivity of +0.02 mmHg/degree C. The pressure sensor comprises a sensing membrane 127 substantially located in the central area 126 on its bottom face 122. Integration in the sensor assembly 100 of other types of sensors for measuring various conditions such as pressure, temperature, pH, blood flow, oxygen saturation and the like, may be contemplated.

In the same or another embodiment, the stiffener 170 may be made of a conductive material. Providing an electrical connection between the stiffener 170 and the conductive cover 160 allows forming an enhanced Faraday-like shield that may absorb most of the parasitic effects caused by chemical conditions in the body in which the sensor assembly 100 is inserted. Such electrical connection may be realized at various points of the sensor assembly 100 by ensuring that the conductive cover 160 reaches the stiffener 170, for example on a lateral side 102 (FIG. 3) of the sensor assembly 100 or on a forward end 162 of the conductive cover 160 (FIG. 4). Various other locations for establishing an electrical contact between the conductive cover 160 and the stiffener 170 may be contemplated.

Generally speaking, the sensor assembly 100 is sized for insertion under the skin of a patient, for acquiring measurements from a body part of the patient. In the non-limiting embodiment of FIGS. 3, 4 and 5, an overall width 'W' of the sensor assembly 100 does not exceed about 1.9 mm, an overall height 'H' of the sensor assembly 100 does not exceed about 1.8 mm, and an overall length of the sensor assembly as measured from a rear-end of the polymer shell 150 to a forward-end of the stiffener 170 does not exceed about 14.0 mm.

Figure 7:
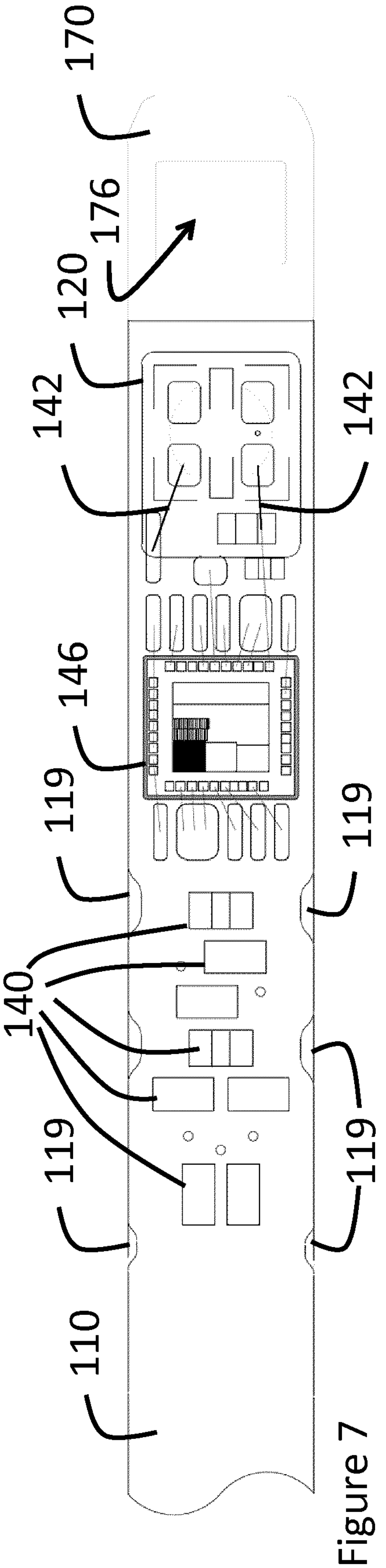
FIG. 7 is a detailed view of surface mounted technology (SMT) components mounted on a top surface of a board according to an embodiment.
Figure 8:
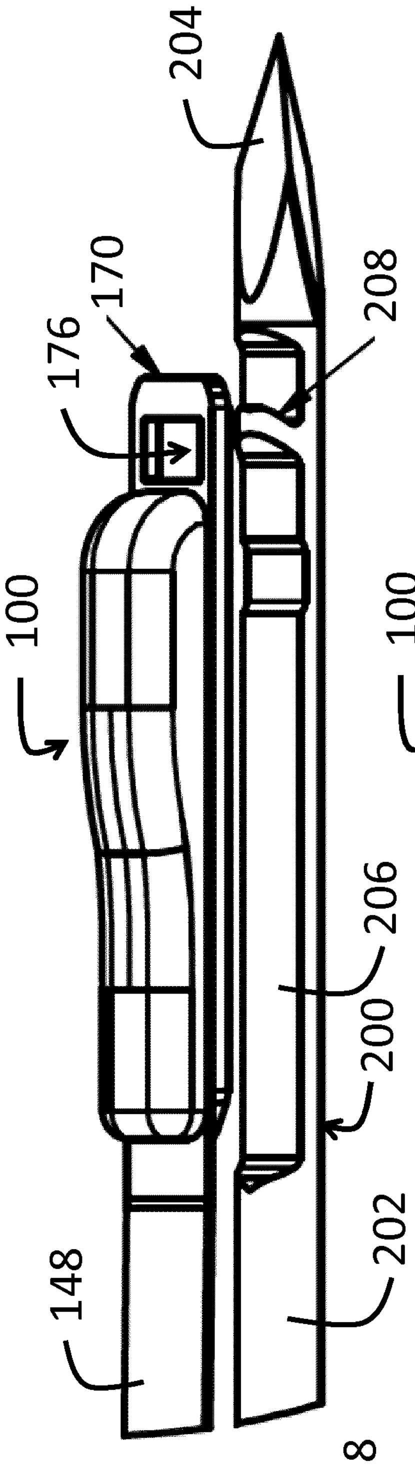
FIG. 8 is a perspective view of the implantable sensor assembly and of a forward end of an insertion device, unassembled according to an embodiment.
Figure 9:
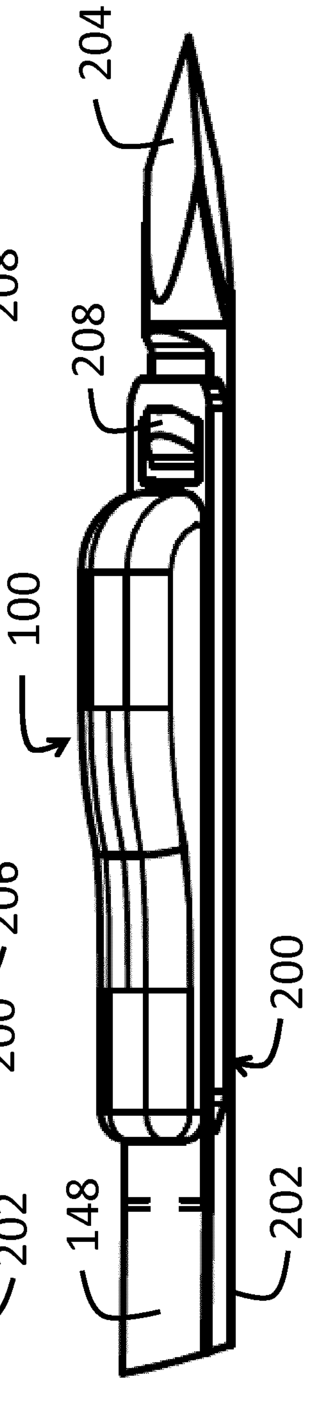
FIG. 9 is a perspective view of the implantable sensor assembly and of the forward end of the insertion device, assembled according to an embodiment.

FIG. 7 is a detailed view of surface mounted technology (SMT) components mounted on a top surface of a board according to an embodiment. Notches 119 are provided on both sides the board 110. These notches 119 are filled when the polymer shell 150 is formed by the application of the liquid or viscous product. At least one SMT component 140 is operatively connected to the sensor 120. As illustrated on FIG. 4, one such component is a converter 146 that is directly connected to the sensor 120 via the wire bonds 142. The converter 146 converts measurement from the sensor 120 into digital signals that are communicated from the sensor assembly 100 to an external device (for example the external module 48 of FIG. 1) via a cable 148 (FIGS. 8 and 9). The converter 146 may be an application-specific integrated circuit (ASIC). In the particular example in which the SCB10H-B012FB capacitive pressure sensor is used, the converter 146 may be a PCap04™ capacitance-to digital converter from AMS AG. Some of the other SMT components 140 process the digital signals from the converter 146 for their transmission via the cable 148. Processes performed by the various SMT components 140 may include, without limitation, filtering, buffering, digital signal processing, temperature compensation, and amplifying of the digital signals. In an embodiment, the measurement from the sensor 120 may be converted to digital form using a delta sigma modulator. In the same or another embodiment, the converter 146 may store calibration coefficients that are used to convert the measurement from the sensor 120 to a pressure value, the calibration coefficients being determined during calibration by performing a polynomial fit of the capacitive pressure sensor as a function of pressure and temperature.

The stiffener 170 includes a hook hole 176 allowing to connect the sensor assembly 100 to an insertion device. FIG. 8 is a perspective view of the implantable sensor assembly and of a forward end of an insertion device, unassembled. FIG. 9 is a perspective view of the implantable sensor assembly and of the forward end of the insertion device, assembled. Considering FIGS. 8 and 9, an insertion device 200 having an elongated member 202 is an evolution of the puncture device 20 introduced in the foregoing description of FIGS. 1 and 2. Only a forward end of the elongated member 202 is shown on FIGS. 8 and 9. The elongated member 202 terminates at a puncturing end 204 for puncturing skin to allow insertion of the sensor assembly 100 in a body. The elongated member 202 also includes a recess 206 adapted for receiving the sensor assembly 100 prior to insertion in the body. A forward facing hook 208 protrudes from the recess 206 and is sized, positioned and configured for being inserted in the hook hole 176 of the stiffener 170 when the sensor assembly 100 is received in the recess 206 of the insertion device 200. The mating of the hook 208 and of the hook hole 176 provides for maintaining a connection of the sensor assembly 100 and of the insertion device 200 when assembled, the cable 148 along a length of the elongated member 202. After insertion of the sensor assembly 100 and of the forward end of the insertion device 200 in the body, the sensor assembly 100 may be disengaged from the insertion device 200 by rotating the insertion device 200.

Without limitation, the sensor assembly 100 and the insertion device 200 may be integrated in the system of FIG. 1. The sensor assembly 100 and the insertion device 200 may otherwise be combined with other systems and used in distinct applications.

Figure 10:
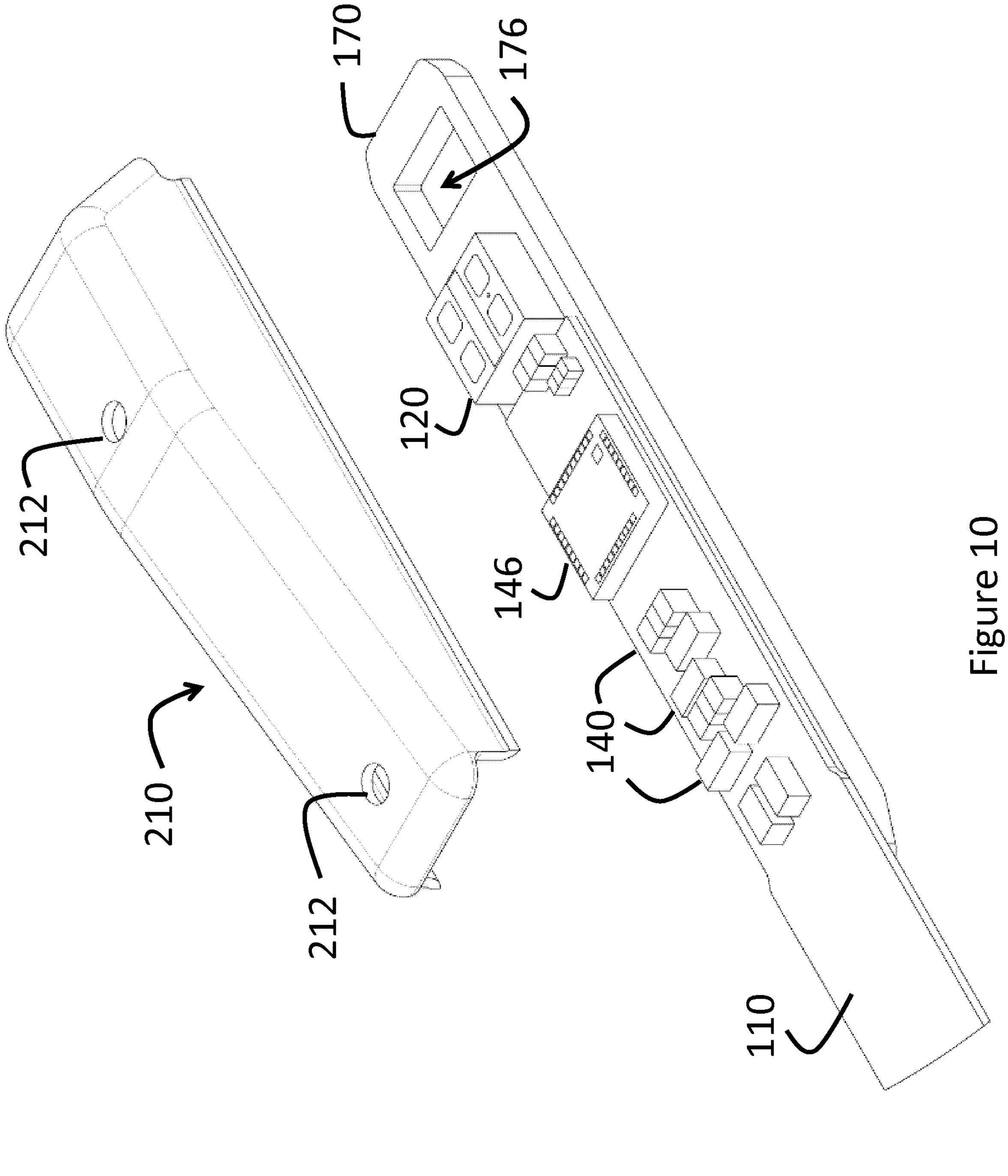
FIG. 10 is a perspective, exploded view of a variant of the implantable sensor according to an embodiment.

FIG. 10 is a perspective, exploded view of a variant of the implantable sensor according to an embodiment. In this embodiment, the polymer shell 150, which is part of the support structure for the sensor assembly 100, and the conductive cover 160 applied on the polymer shell 150 are replaced by a rigid cap 210 that fits on the board 110 over the sensor 120, the converter 146 and the SMT components 140. The cap 210 makes contact with the stiffener 170 to complete the support structure with the board 110. The cap 210 and the stiffener 170 may be permanently attached to one another, for example by seam welding, laser welding, or ultrasonic welding.

In an embodiment of the sensor assembly 100, the cap 210 may have one or more holes 212. These holes 212 may optionally be used to inject a predetermined amount of a gel compound to fill at least in part a cavity formed between the cap 210 and the top surface 114 of the board 110, which would be filled by the polymer shell 150 in the embodiment of as shown on FIG. 4. The cavity, which is not shown on FIG. 10, has the same or equivalent shape as that of the polymer shell 150 of FIG. 4.

The cap 210 and the stiffener 170 may be made of conductive materials so that the enclosure formed thereby becomes another Faraday-like shield that minimizes the sensitivity of the sensor to variations in the dielectric constant of its environment.

The cap 210 may be manufactured, for example, by a low-cost, high-speed process, for example using a stamping process. The cap 210 may thus replace the combination of the polymer shell 150 and of the conductive cover 160 while increasing manufacturability, uniformity, and yield of the sensor assembly 100.

An embodiment of the sensor assembly 100 that includes the cap 210 provides added flexibility in the manner in which the sensor 120 is mounted on the board 110. For example, the sensor 120 may be mounted on the board 110 in the same manner as illustrated in FIG. 6, with the sensing membrane 127 facing down, positioned above the through apertures 112 and 174 of the board 110 and of the stiffener 170 and thus exposed to the external environment. Alternatively, as shown on FIG. 11, which is a perspective, exploded view of another variant of the implantable sensor according to an embodiment, the sensor 120 may be mounted with the sensing membrane 127 facing up, away from the board 110, the sensing membrane 127 being thus disposed on the top face of the sensor 120. Also in the embodiment of FIG. 11, the through apertures 112 and 174 of the board 110 and of the stiffener 170 may be omitted and another top aperture 214 may be made in the cap 210 to expose the sensing membrane 127 to the external environment.

In an embodiment, electrical connections between the sensor 120 and traces on the board 110 for connection to the SMT components 140 may be made using solder paste on the board 110, obviating the need for at least some of the wire bonds 142 and allowing for a reduction in the height of the rigid cap 210. In another embodiment, an electrically conductive ink traces may be used instead of the solder paste traces. In comparison with solder paste, the conductive ink is softer and has a lower temperature coefficient of expansion, reducing thermal stresses that may be transmitted to the sensor 120. Use of a combination of the wire bonds 142, solder paste traces and electrically conductive ink traces for connecting the various SMT components 140 to the sensor 120 is also contemplated.

Figure 11:
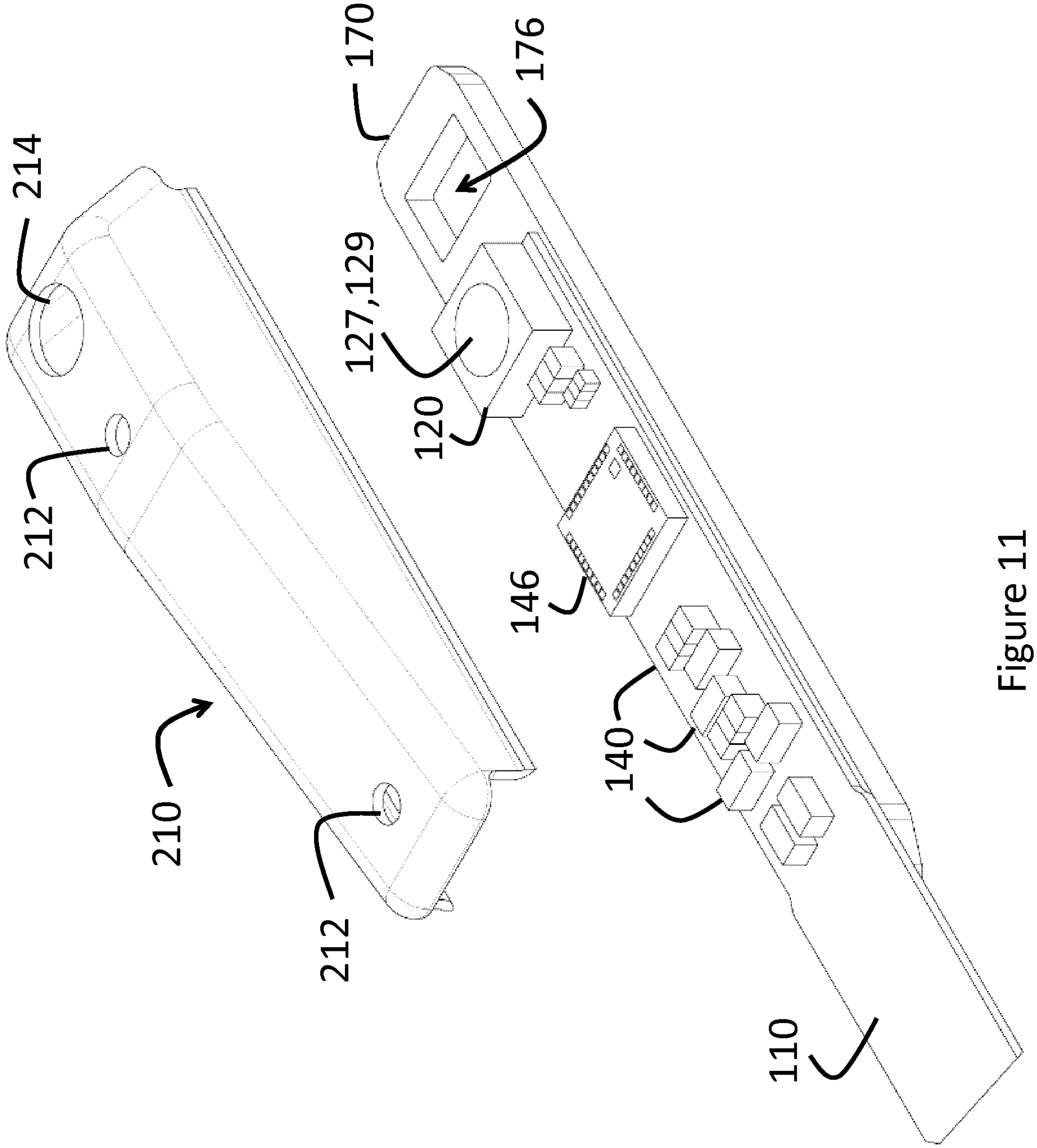
FIG. 11 is a perspective, exploded view of another variant of the implantable sensor according to an embodiment.

In the embodiment of FIG. 10, in which the sensor 120 is mounted with the sensing membrane 127 facing down, the through aperture 112 or 174 may form a volume in which air bubbles may be trapped when the sensor assembly 110 is inserted into the body. In the embodiment of FIG. 11, in which the sensor 120 is mounted with the sensing membrane 127 facing up (i.e. on the top face of the sensor 12), the rigid cap 210 may be configured to be flush with the sensing membrane 127 in order to avoid presence of such a volume and to prevent the formation of air bubbles when the sensor assembly 110 is inserted into the body. As such, the lips 132 of the compliant structure 130 may extend along a periphery of the top aperture 214 of the cap 210 and along a periphery of the sensing membrane 127 disposed on the top face of the sensor 120, the portions 134 and 136 being disposed in a reverse orientation from that shown on FIG. 6. In a variant of the configuration illustrated on FIG. 11, the upper and lower portions 134 and 136 of the compliant structure 130 may be replaced with a single gel compound. In this variant, the cavity formed by the cap 210, the board 110 and the stiffener 170 may be filled with a single gel, the lips 132 of the compliant structure 130 being used to provide an interface between the sensor 120 and the cap 210.

In an embodiment of the sensor assembly 100, the sensing membrane 127 of the sensor 120 may be protected from the dielectric environment by adding a layer of hydrophobic material 129 disposed upon the sensing membrane 127. The hydrophobic material may serve as a barrier to prevent water ingress into the sensor 120 while maintaining a stable value for the dielectric constant at the sensing membrane 127, despite variations in the dielectric constant of the medium into which the sensor 120 is inserted. In one embodiment, the hydrophobic material may for example and without limitation be parylene or a Gel 8251. In another embodiment, the layer of hydrophobic material 129 may comprise a multilayer coating with plural layers of a polymer and of a dielectric material. For example and without limitation, the multilayer coating may comprise one or more parylene C polymer layers and one or more silicon oxide dielectric layers that may be deposited using chemical vapor deposition. On the one hand, while the high molecular density silicon oxide dielectric layer(s) may have lower permeability, they may increase internal stress formation. On the other hand, the parylene C polymer layer(s) may act as stress-relieving layer(s) while having higher permeability. The multilayer coating that combines layers of both materials may at once provide low stress and low permeability coating on the sensing membrane 127.

Some applications may use an implantable sensor that, while not particularly impacted by temperature variations, may still benefit from protection against parasitic effects caused by chemical conditions in the body. Embodiments of the sensor assembly 100 may include the sensor 120 being mounted on the top surface 114 of the board 110, without the compliant structure 130. The sensor 120 may be directly mounted to the top surface 114 of the board 110 or may be mounted indirectly, in a manner that does not allow the sensor 120 to float. As an example, the sensor 120 may itself be an SMT component and be bonded directly to the board 110, being connected to the other SMT components 140 without the use of wire bonds 142. In embodiments without the compliant structure 130, the sensor assembly 100 comprises the stiffener 170, as well as either the polymer shell 150 applied on the top surface of the board and the conductive cover 160 applied on the polymer shell 150, or the cap 210 mounted onto the board 110, so that the polymer shell 150 or the cap 170 encloses the sensor 120. In one such embodiment, the board 110 and the stiffener 170 may respectively include the through apertures 112 and 174 to allow exposure of the bottom face 122 of the sensor 120. In the same or another such embodiment, the sensor assembly 100 may include the SMT components 140, for example the converter 146, and the cable 148. In the same or another embodiment, the stiffener 170 is made of a conductive material and is electrically connected to the conductive cover 160 or to the cap 210 to form a Faraday-like shield that may absorb most of the parasitic effects caused by chemical conditions in the body in which the sensor assembly 100 is inserted.

EXAMPLES

Measurements were obtained using a conventional pressure sensor and a pressure sensor mounted in the compliant structure 130. Long-term drift over a period of more than 25 hours was measured at about 9 mmHg when using the conventional pressure sensor, compared to about 2 mmHg when using the sensor 120 mounted in the compliant structure 130.

Other measurements were obtained using a conventional pressure sensor and a pressure sensor enclosed within the conductive cover forming the Faraday-like shield. In deionized water, the absence of the conductive cover introduced an offset of 14 mmHg in the measured value. After addition of the conductive cover, the pressure was within the measurement tolerance.

Those of ordinary skill in the art will realize that the description of the implantable sensor assembly is illustrative only and are not intended to be in any way limiting. Other embodiments will readily suggest themselves to such persons with ordinary skill in the art having the benefit of the present disclosure. Furthermore, the disclosed implantable sensor assembly may be customized to offer valuable solutions to existing needs and problems related to the exposure of implantable biocompatible sensors to various physical conditions. In the interest of clarity, not all of the routine features of the implementations of the implantable sensor assembly are shown and described. In particular, combinations of features are not limited to those presented in the foregoing description as combinations of elements listed in the appended claims form an integral part of the present disclosure. It will, of course, be appreciated that in the development of any such actual implementation of the implantable sensor assembly, numerous implementation-specific decisions may need to be made in order to achieve the developer's specific goals, such as compliance with application-related, system-related, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of implantable sensors having the benefit of the present disclosure.

The present disclosure has been described in the foregoing specification by means of non-restrictive illustrative embodiments provided as examples. These illustrative embodiments may be modified at will. The scope of the claims should not be limited by the embodiments set forth in the examples, but should be given the broadest interpretation consistent with the description as a whole.

What is claimed is:

1. An implantable sensor assembly, comprising:

a printed circuit board comprising a first aperture through the printed circuit board;

a stiffener mounted on a bottom surface of the printed circuit board, the stiffener comprising a second aperture through the stiffener aligned with the first aperture of the printed circuit board;

a compliant structure formed of one or more materials capable of elastic deformation disposed on a top surface of the printed circuit board;

a sensor, which is adapted to measure one or more of temperature, humidity, pressure and potential hydrogen (pH), with a bottom face supported by the compliant structure above the top surface of the printed circuit board, opposite to the bottom face surface of the printed circuit board that is joined to the stiffener, wherein at least in part the bottom face of the sensor is configured to be exposed through the second aperture of the stiffener and through the first aperture of the circuit board through lips of the compliant structure that extend between a perimeter of the bottom face of the sensor and the top surface of the circuit board;

a polymer shell enclosing the sensor, except for the bottom face of the sensor; and a conductive cover applied on the polymer shell, wherein:

the stiffener is made of a conductive material; and the stiffener is electrically connected to the conductive cover by having the stiffener reach the conductive cover.

2. The sensor assembly of claim 1, wherein the compliant structure comprises:

a first portion formed of a first gel compound disposed on a first top face of the sensor opposite the bottom face; and a second portion formed of a second gel compound surrounding the sensor and extending between the first gel compound and the bottom face of the sensor that is at least in part configured to be exposed, the lips being part of the second portion.

3. The sensor assembly of claim 2, wherein the first gel compound has a first viscosity and the second gel compound has a second viscosity greater than the first viscosity.

4. The sensor assembly of claim 1, further comprising:

at least one surface mounted technology (SMT) component mounted on the circuit board and operatively connected to the sensor, the at least one SMT component comprising a converter adapted to convert the measurements from the sensor into digital signals; and a cable extending from the at least one SMT component and adapted to communicate measurements from the sensor to an external device.

5. The sensor assembly of claim 4, wherein the polymer shell encloses the at least one SMT component, the sensor and the compliant structure.

6. The sensor assembly of claim 1, wherein the conductive cover comprises a layer of conductive ink.

7. The sensor assembly of claim 4, wherein the compliant structure fully covers all faces of the sensor other than the bottom face of the sensor that is at least in part configured to be exposed while allowing passages of electrical connections between the sensor to the at least one SMT component.

8. The sensor assembly of claim 4, wherein electrical connections between the at least one SMT component and the sensor each comprise one or more elements selected from wire bonds, solder paste traces on the circuit board, conductive ink traces on the circuit board, and a combination thereof.

9. The sensor assembly of claim 1, wherein the sensor is a pressure sensor comprising a sensing membrane exposed at least in part to the aperture formed in the circuit board.

10. The sensor assembly of claim 9, further comprising a layer of hydrophobic material disposed on the sensing membrane.

11. The sensor assembly of claim 1, wherein the stiffener has a hook hole adapted for mating with a hook of an insertion device.

12. The sensor assembly of claim 1, wherein the aperture is circular.

13. An implantable sensor assembly, comprising:

a printed circuit board comprising a first aperture;

a stiffener mounted on a bottom surface of the printed circuit board, the stiffener comprising a second aperture aligned with the first aperture of the printed circuit board;

a compliant structure formed of one or more materials capable of elastic deformation disposed on a top surface of the printed circuit board;

a sensor, which is adapted to measure one or more of temperature, humidity, pressure and potential hydrogen (pH), with a bottom face supported by the compliant structure above the top surface of the printed circuit board, opposite to the bottom surface of the printed circuit board that is joined to the stiffener, wherein at least in part the bottom face of the sensor is configured to be exposed through the second aperture of the stiffener and the first aperture of the circuit board;

a polymer shell enclosing the sensor, except for the bottom face of the sensor; and a conductive cover applied on the polymer shell, wherein:

the stiffener is made of a conductive material; and the stiffener is electrically connected to the conductive cover by having the stiffener reach the conductive cover.

* * * * *